US005527772A

United States Patent [19]
Holick

[11] Patent Number: 5,527,772
[45] Date of Patent: Jun. 18, 1996

[54] REGULATION OF CELL PROLIFERATION AND DIFFERENTIATION USING PEPTIDES

[76] Inventor: Michael F. Holick, 31 Bishop La., Sudbury, Mass. 01776

[21] Appl. No.: 281,648

[22] Filed: Jul. 28, 1994

Related U.S. Application Data

[62] Division of Ser. No. 118,692, Sep. 10, 1993, abandoned, which is a continuation of Ser. No. 575,219, Aug. 30, 1990, abandoned, which is a continuation-in-part of Ser. No. 110,973, Oct. 20, 1987, abandoned.

[51] Int. Cl.$^6$ .................. A61K 38/29; C07K 14/635
[52] U.S. Cl. .................................... 514/12; 530/324
[58] Field of Search ................... 514/12.21; 530/324

[56] References Cited

U.S. PATENT DOCUMENTS 5,093,233  3/1992  Rosenblatt et al. ............... 530/324
5,120,831  6/1992  Pickart ............................... 530/329

FOREIGN PATENT DOCUMENTS 190018   8/1986   European Pat. Off. ............ 514/2
336760  10/1989   European Pat. Off. ............ 514/12

OTHER PUBLICATIONS

Endocrinology, vol. 118, No. 6, issued 1986, MacDonald et al, "Parahyroid Hormone Stimulates The Proliferation ...", pp. 2445–2449.

Biological Abstracts, vol. 81, No. 2, issued 15 jan. 1986, Partridge et al, "Inhibitory Effects of Parathyroid Hormone ...", Abstract No. 15489.

Endocrinology, vol. 108, No. 1, issued 1981, Bringhurst et al, "Bone Collagen Synthesis in Vitro ...", pp. 103–108.

Endocrinology, vol. 123, No. 6, issued 1988, Fukagama et al. "Human Parathyroid Hormone (PTH)–Related Protein ...", pp. 2841–2848.

J. Clin. Invest., vol 81, issued Mar. 1988, Rodan et al, "Comparison of Postreceptor Effects ...", pp. 924–927.

J. Clin. Invest. vol. 81, issued Mar. 1988, Yates et al, "Effects of a Synthetic Peptide ...", pp. 932–938.

Science, vol. 231, isued 24 jan. 1986, Merendino et al, "A Parathyroid Hormone–Like Protein ...", pp. 388–390.

PNAS USA, vol. 83, issued Oct. 1986, Doppelt et al, "Inhibition of the in vivo parathyroid hormone ...", pp. 7557–7560.

Clinical Research, vol. 37, No. 2, issued Apr. 1989, Holick et al, "Synthetic Fragments of 8th–Related Peptide ...", p. 529A.

J. Cell Biology, vol. 107(6part 3), issued Dec. 1988, Nolick et al, "8th Related Peptide ...", p. 40a, abstract No. 202.

Primary Examiner—Jeffrey E. Russel
Attorney, Agent, or Firm—Sterne, Kessler, Goldstein & Fox

[57] ABSTRACT

Disclosed are methods of inhibiting proliferation and enhancing differentiation of a mammalian cell, inducing proliferation of a mammalian cell, enhancing wound healing, and stimulating hair growth using a peptide which has 10% or greater homology to a region of human parathyroid hormone or human hypercalcemic factor.

12 Claims, 8 Drawing Sheets

```
              -30             -20             -10              1              10
hPTHrP   MQRRLVQQWSVAVFLLSYAVPSCGRSVEGLSRRLKRAVSEHQLLHDKGKS
hPTH     -----MIPAKDMAKVMIVMLAICFLTKSDGKSVKKRSVSEIQLMHNLGKH
bPTH     -----MMSAKDMVKVMIVMLAICFLARSDGKSVKKRAVSEIQFMHNLGKH
pPTH                         KPIKKRSVSEIQLMHNLGKH
rPTH     -----MMSASTMAKVMILMLAVCLLTQADGKPVKKRAVSEIQLMHNLGKH 20              30              40              50              60
hPTHrP   IQDLRRRFFLHHLIAEIHTAEIRATSEVSP-NSKPSPNTKNHPVRFGSDD
hPTH     LNSMERVEWLRKKLQDVHNFVALGAPLAPRDAGSQRPRKKEDNVLVESHE
bPTH     LSSMERVEWLRKKLQDVHNFVALGASIAYRDGSSQRPRKKEDNVLVESHQ
pPTH     LSSLERVEWLRKKLQDVHNFVALGASIVHRDGGSSQRPRKKEDNVLVESHQ
rPTH     LASVERMQWLRKKLQDVHNFVSLGVQMAAREGSYQRPTKKEENVLVDGNS 70              80              90             100             110
hPTHrP   EGRYLTQETNKVETYKEQPLKTPGKKKKGKPGKRKEQEKKKRRTRSAWLD
hPTH     KSLGEADKADVNVLTKAKSQ
bPTH     KSLGEADKADVLIKAKPQ
pPTH     KSLGEADKAAVDVLIKAKPQ
rPTH     KSLGEGDKADVDVLVKAKSQ 120             130             140
hPTHrP   SGVTGSGLEGDHLSDTSTTSLELDSRRH
```

FIG. 1

REGULATION OF CELL PROLIFERATION AND DIFFERENTIATION USING PEPTIDES

This application is a division of application Ser. No. 08/118,692, filed Sep. 10, 1993, now abandoned, which is a continuation of application Ser. No. 07/575,219, filed Aug. 30, 1990, now abandoned, which is a continuation-in-part of application Ser. No. 07/110,973, filed Oct. 20, 1987, now abandoned.

BACKGROUND OF THE INVENTION

This invention relates to the regulation of cell differentiation and proliferation, e.g., for treating hyperproliferative skin disorders, such as psoriasis, for enhancing wound healing, and for stimulating hair growth.

Psoriasis is a disease of the epidermis and a major cause of disability and disfigurement for between 1 to 3% of the population of the world. In the United States approximately 2,000,000 to 8,000,000 persons suffer from this disorder, and approximately 100,000 are severely affected.

The disease is diagnosed by the presence of scaling, erythematous lesions on the scalp and extensor aspects of the arms and legs. Psoriatic lesions often are accentuated at sites of repeated trauma such as the elbows and knees. Furthermore, this skin disorder can afflict most of the areas of the skin of some individuals and can also cause internal damage such as arthritis. This disease is characterized by a hyperproliferation of the basal cells (a several fold increase in the number of basal cells of the epidermis). This increase in the basal cell population reduces the turnover time of the epidermis from the normal 27 days to 3-4 days. This shortened interval prevents normal cell maturation and keratinization, and this failure of maturation is reflected in an array of abnormal morphologic and biochemical changes. Numerous cytologic, histologic, histochemical, and biochemical alterations are known to be the result, rather than the cause, of the disease process.

The treatment of psoriasis still remains the province of dermatologists. The most effective treatment for the control of localized psoriasis for most patients is the topical use of corticosteroids with a plastic wrap, ultraviolet light treatments, and sunlight exposure. For certain patients with generalized psoriasis, it has been necessary to use a variety of systemic chemotherapeutic agents, especially methotrexate; the latter has the capacity to inhibit cell replication without a proportionate inhibition of cell function. Photochemotherapy was introduced in 1974, the so-called PUVA treatment. This treatment consists of administering psoralen prior to partial or whole body irradiation with a special light system that emits predominately long wave length ultraviolet light (UV-A).

Recently, it has been appreciated that the skin is not only the site for the synthesis of vitamin D, but is also a target tissue for its biologically active form, 1,25-dihydroxyvitamin $D_3$ (1,25$(OH)_2D_3$). A variety of tumor cells (for example, HL-60, U937, and M-1), as well as normal cells (such as activated T-lymphocytes, monocytes, cultured skin fibroblasts, keratinocytes, and cells isolated from the skin of rats, mice, and humans contain a high affinity ($1.0 \times 10^{-10}$M), low capacity, protein which is a receptor for 1,25$(OH)_2D_3$. For tumor cells that possess a receptor for 1,25$(OH)_2D_3$, the hormone inhibits their proliferation and induces them to differentiate (Suda et al. in Vitamin D: Chemical, Biochemical and Clinical Update (Norman et al., ed.) Walter de Gruyter N. Y. 1985 pp. 187–196). 1,25$(OH)_2D_3$ inhibits the proliferation of cultured human fibroblasts and keratinocytes and induces keratinocytes to terminally differentiate (Smith et al., J. Invest. Dermatol. 86:709–714, 1986). It has been demonstrated that 1,25$(OH)_2D_3$ and its analog 1,24-dihydroxyvitamin $D_3$ are of value in the treatment of psoriasis when provided either orally or topically (Morimoto et al. Brit. J. Dermatol. 115:421–429, 1986; Kato et al. Brit. J. Dermatol. 115, 431–433, 1986).

Aging is associated with a variety of changes in the skin. There is an age-related decrease in epidermal turnover rate of approximately 30 to 50% between the 3rd and 8th decades. Thymidine labeling index (a measure of the proliferative activity of cells) of the epidermis in vivo has been reported to decline nearly 50% with age from approximately 5.1% in 19–25 year old men to approximately 2.85% in 69–85 year old men. Additional investigations have revealed that there is a 100% prolongation in stratum corneum replacement rate in old verses young men (Gilchrest, B. in Skin and Aging Processes, CRC Press, p. 21, 1984).

Parathyroid hormone (PTH), a polypeptide 84 amino acids long, plays an important role in the maintenance of the concentration of ionized calcium in extracellular fluids within normal range. Parathyroid hormone acts directly to raise extracellular calcium by its effects on the bone and kidney, and indirectly by increasing the production of 1,25$(OH)_2D_3$ to enhance intestinal calcium absorption (Krane S. M. and Potts, J. T. in Harrison's Textbook Principles of Internal Medicine, 9th ed., pp. 1824–1832, 1980). A variety of cells, including kidney cells, lymphocytes, and osteosarcoma cells, possess receptors for parathyroid hormone (Yamamoto, I. et al., J. Clin. Invest. 71:404–407, 1983; Goldring, S. et al., J. Clin. Endo. and Met. 46:425–433, 1978). A variety of in vitro and in vivo tests have been developed to assay for parathyroid hormone. These include the measurement of cyclic AMP production in isolated canine kidney membranes (Nissenson et al., J. Clin. Endo. and Met. 52:840, 1981) and in osteosarcoma cells (Lindall, A. W. et al., J. Clin. Endo. and Met. 57:1007, 1983) and human fibroblasts (Goldring et al., J. Clin. Endo. and Met. 46:425–433, 1978). A cytochemical assay has also been developed to measure glucose-6-phosphate dehydrogenase activity in guinea pig kidney (Goltzman, D. J. et al., Clin. Invest. 65:1309, 1980). In addition, a multiresponse parathyroid hormone assay has been developed to measure both agonist and antagonist properties of parathyroid hormone analogs (Horiuchi, N. et al. Am. J. Physiol. 244:E589–595, 1983).

A variety of PTH analogs have been made. Of interest has been the observation that a 34-residue amino terminal fragment of the PTH molecule [PTH (1-34)] is biologically active in vitro and in vivo (Nussbaum, S. R. et al. J. Prot. Chem. 4:391–406, 1985). Rat PTH (1-34), which has a 5 amino acid sequence difference from the corresponding 1-34 region of both human and bovine PTH, has been found to be 8–10 fold more active than human PTH (1-34) and 2-4 fold more active than bovine PTH (1-34) in the canine adenylate cyclase system (Keutmann, H. T. et al. Endocrinol. 117:1230, 1985). Structure activity studies revealed that PTH-stimulated biologic responses in vitro can be inhibited by [$Nle^8$, $Nle^{18}$, $Tyr^{34}$] bovine PTH (3-34) PTH amide (bPTH (3-34)). The parathyroid hormone analog [$Tyr^{34}$] bovine PTH-(7-34)-amide can inhibit the PTH-mediated elevation of plasma calcium in thyroparathyroidectomized rats in vivo, and is devoid of PTH-like agonist activity (Doppelt, S. H. et al. Proc. Natl. Acad. Sci. USA. 83;7557, 1986).

Recently, it has been found that cultured human keratinocytes make a parathyroid hormone-like protein, referred to herein as "hypercalcemic factor" (Merendino, J. J. et al. Science 231:388–390 1986). Keratinocyte-conditioned medium was harvested from confluent, first passage cultures. Conditioned medium from each of 10 keratinocyte cultures stimulated adenylate cyclase activity in a clonal ROS 17-2.8 cell assay. This biologically active substance is thought to be one of the factors responsible for causing humoral hypercalcemia in patients with a variety of malignancies. This PTH-related protein was isolated from a human lung cancer cell line, and full-length complementary DNA clones encoding it have been inserted into expression vectors used to produce the peptide in mammalian cells. The clones were found to encode a prepropeptide of 36 amino acids and a mature protein of 141 amino acids that has significant homology with parathyroid hormone in the amino terminal region; of the first 16 residues of this protein, 8 of the 16 were found to be identical to human PTH (Suva, L. J. et al. Science 232:893–896, 1987). FIG. 1 herein, reproduced from FIG. 2 of Suva et al., gives the sequences of the two proteins.

SUMMARY OF THE INVENTION

The aforementioned seemingly divergent lines of research, i.e., the use of $1,25(OH)_2D_3$ for the treatment of psoriasis based on its ability to inhibit keratinocyte proliferation and induce terminal differentiation, and the observation that cultured human keratinocytes produce the PTH-like-hypercalcemic factor, have been brought together in the present invention.

This invention arose in part out of the following discoveries: 1) when human cultured keratinocytes are incubated with human PTH (1-34) (herein, PTH (1-34)) at $10^{-7}$ and $10^{-8}$M, this polypeptide fragment inhibits growth and induces terminal differentiation of these cells; 2) a synthetic fragment of hypercalcemic factor ([$Tyr^{34}$] calcemic factor fragment (1-34) amide (herein, CFF (1-34)) also inhibits the proliferation and induces terminal differentiation of keratinocytes in a dose-dependent manner at $10^{-10}$, $10^{-8}$ and $10^{-7}$M concentrations; 3) [$Nle^8$, $Nle^{18}$, $Tyr^{34}$] bovine (3-34) PTH amide (herein, PTH (3-34)), like PTH (1-34), is an agonist, i.e., it inhibits proliferation and induces terminal differentiation of keratinocytes; 4) [$Tyr^{34}$] bovine PTH (7-34) amide (herein, PTH (7-34)) is an antagonist which blocks the antiproliferative and differentiation-inducing activities of PTH (1-34) and CFF (1-34); 5) the antagonist PTH (7-34) blocks the keratinocyte antiproliferative and terminal differentiation-inducing activities of $1,25(OH)_2D_3$; 6) human PTH (7-34) and human PTH (1-34) enhance wound healing in skin punch assays performed on rats; and, 7) human PTH (7-34) stimulates hair growth in an in vitro hair growth assay.

At the most general level, the invention provides two important therapeutic methods, one involving inhibition of cell proliferation and enhancement of cell differentiation (the agonist activity), which is useful in the treatment of psoriasis, and one involving enhancement of cell proliferation (the antagonist activity), which is useful in wound healing. In addition, the invention provides methods for enhancing wound healing and hair growth based on in vivo wound healing activity or in vitro hair growth activity rather than strict agonist or antagonist activity in vitro.

The first method of the invention generally involves inhibiting proliferation and enhancing differentiation of a mammalian cell by contacting the cell with a peptide (preferably at least 3, and more preferably at least 8, amino acids long) which has 10% or greater (more preferably, 50% or greater, and most preferably 75% or greater) homology with a region (preferably within the amino-terminal 34 amino acid region) of human parathyroid hormone or human hypercalcemic factor, and which is capable of inhibiting proliferation or enhancing the differentiation in vitro of cultured human keratinocytes. In preferred embodiments of this method, the peptide is PTH (1-34), PTH (3-34), or CFF (1-34). This method has particular application in the treatment of hyperproliferative skin disorders such as psoriasis. The method may also be useful in the treatment of certain cancers, by the inhibition of cancer cell proliferation and by the induction of differentiation.

The second method of the invention generally involves enhancing proliferation of a mammalian cell by contacting the cell with a peptide (preferably at least 3, and more preferably at least 8, amino acids long) which has 10% or greater (more preferably, 50% or greater, and most preferably 75% or greater) homology with a region (preferably within the amino-terminal 34 amino acid region) of human parathyroid hormone or human hypercalcemic factor, and which is capable of blocking the differentiation or the inhibition of proliferation in vitro of cultured human keratinocytes by PTH (1-34) or $1,25(OH)_2D_3$ or CFF (1-34). In a preferred embodiment of this method, the peptide is PTH (7-34). In a related method of the invention, proliferation of a mammalian cell, e.g., during wound healing, is enhanced by contacting the cell or wound with a peptide (preferably at least 3, and more preferably at least 8, amino acids long) which has 10% or greater (more preferably, 50% or greater, and most preferably, 75% or greater) homology with a region (preferably, within the amino-terminal 34 amino acid region) of human parathyroid hormone or human hypercalcemic factor, and which is capable of enhancing wound healing in an in vivo skin punch assay. In preferred embodiments of this method, the peptide is PTH (1-34), PTH (7-34), CFF (1-34), or CFF (7-34). These related methods have particular application in the enhancement of wound healing and may also have applications in the promotion of skin growth in patients with burns or skin ulcerations as well as in the stimulation of epidermal regrowth in people who have decreased epidermal cell proliferation due to aging.

Hair growth is stimulated by administering to a mammal a peptide (preferably at least 3, and more preferably at least 8, amino acids long) which has 10% or greater (more preferably, 50% or greater, and most preferably, 75% or greater) homology with a region (preferably, within the amino-terminal 34 amino acid region) of human parathyroid hormone or human hypercalcemic factor, and which is capable of stimulating hair growth in vitro. In a preferred embodiment of this method, the peptide is PTH (7-34). This method can have applications in the promotion of new hair growth or stimulation of the rate of hair growth, e.g., following chemotherapeutic treatment or for treating a form of alopecia, e.g., male pattern baldness.

Other features and advantages of the invention will be apparent from the following description of the preferred embodiments thereof, and from the claims.

DESCRIPTION OF THE PREFERRED EMBODIMENTS

The drawings are first described.

DRAWINGS

FIG. 1 is a comparison of the amino acid sequences of human PTH and hypercalcemic factor, taken from Suva et al., id. This figure shows the homology of PTH-related protein and PTH. The sequences are human PTH-related protein (hPTHrP); human (h), bovine (b), porcine (p) and rat (r) PTH.

FIGS. 2, 3, 4, and 5 are bar graphs showing comparative proliferative effects of peptides of the invention.

SYNTHESIS AND SELECTION OF PEPTIDES

Figure 2:
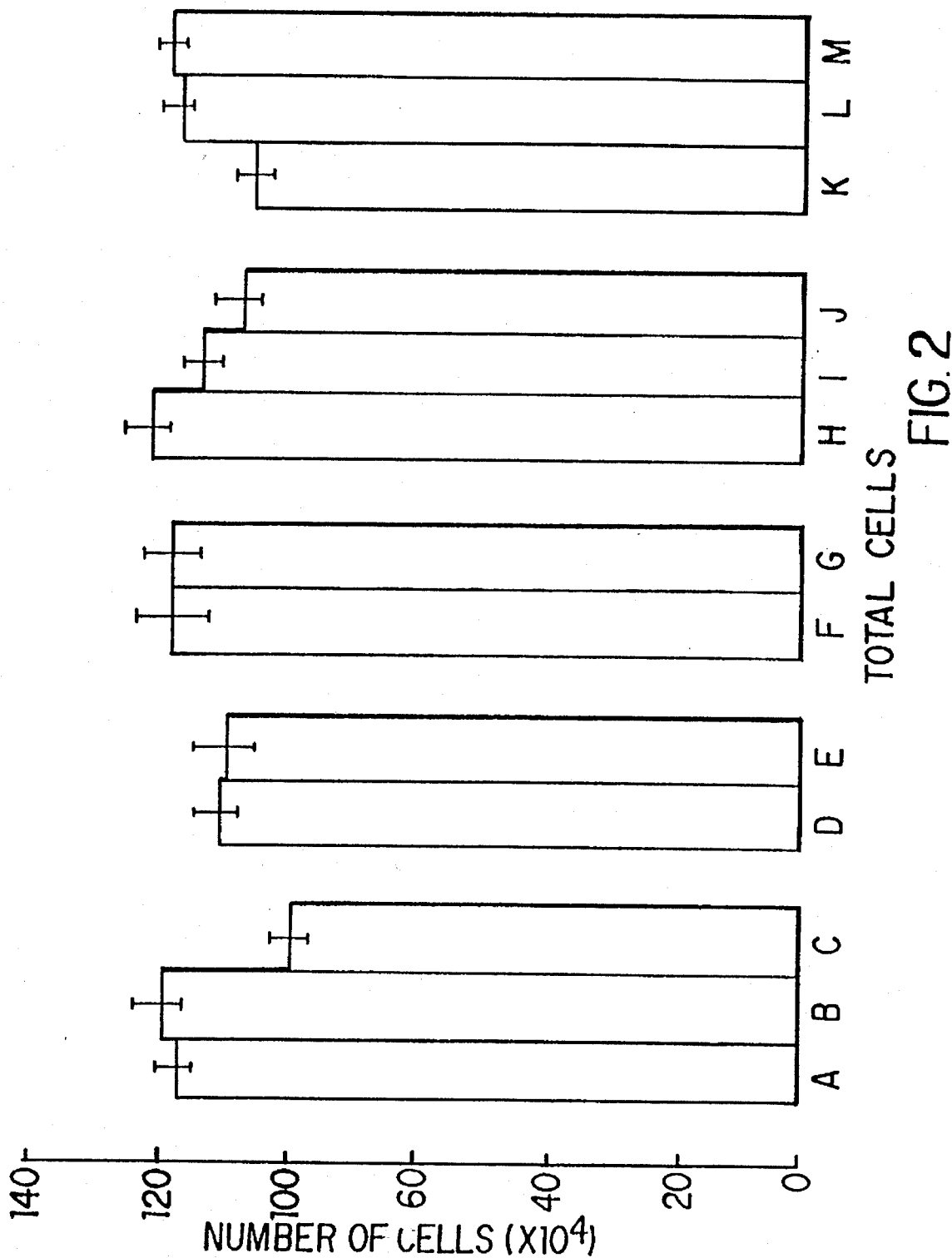
Figure 3:
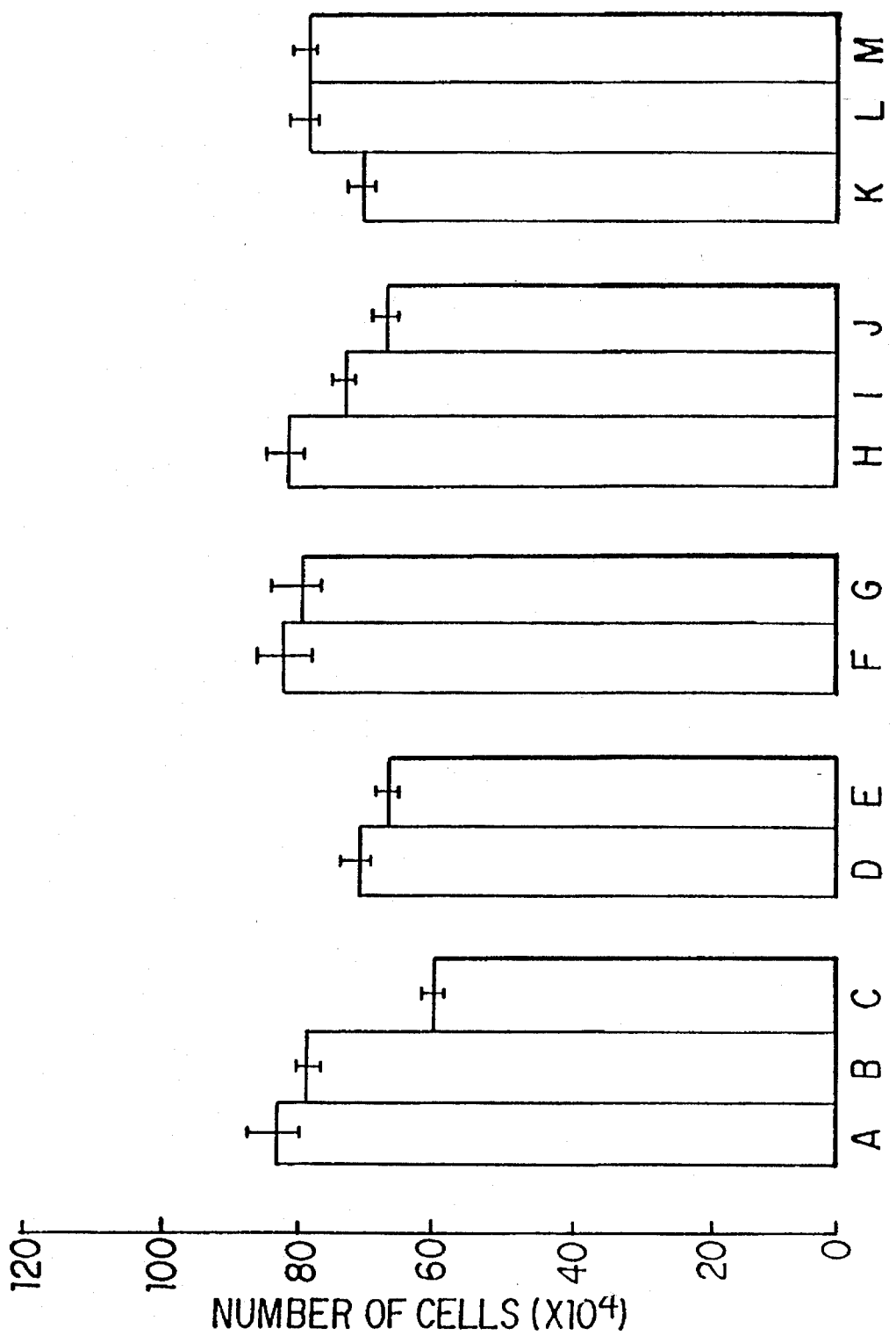
Figure 4:
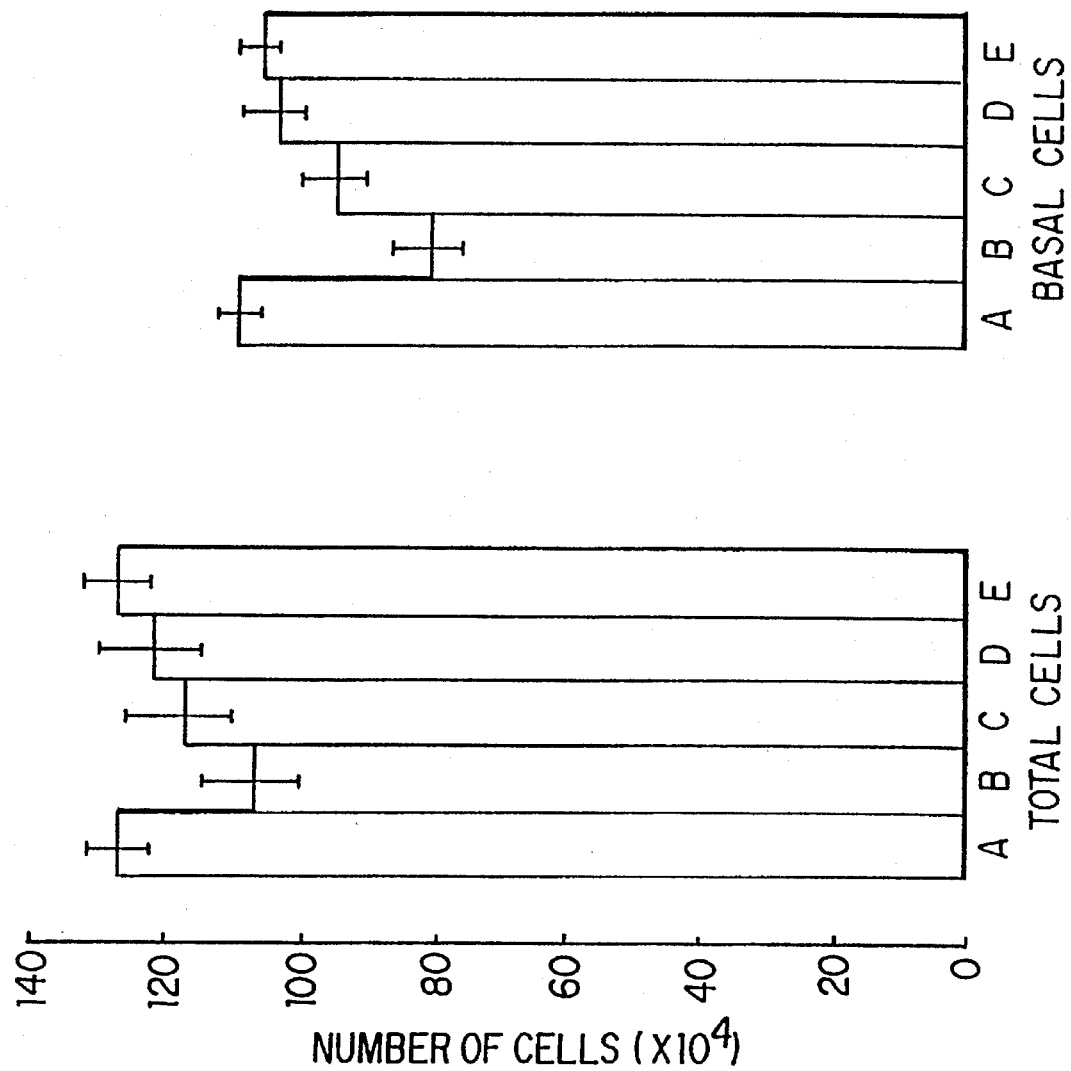
Figure 5:
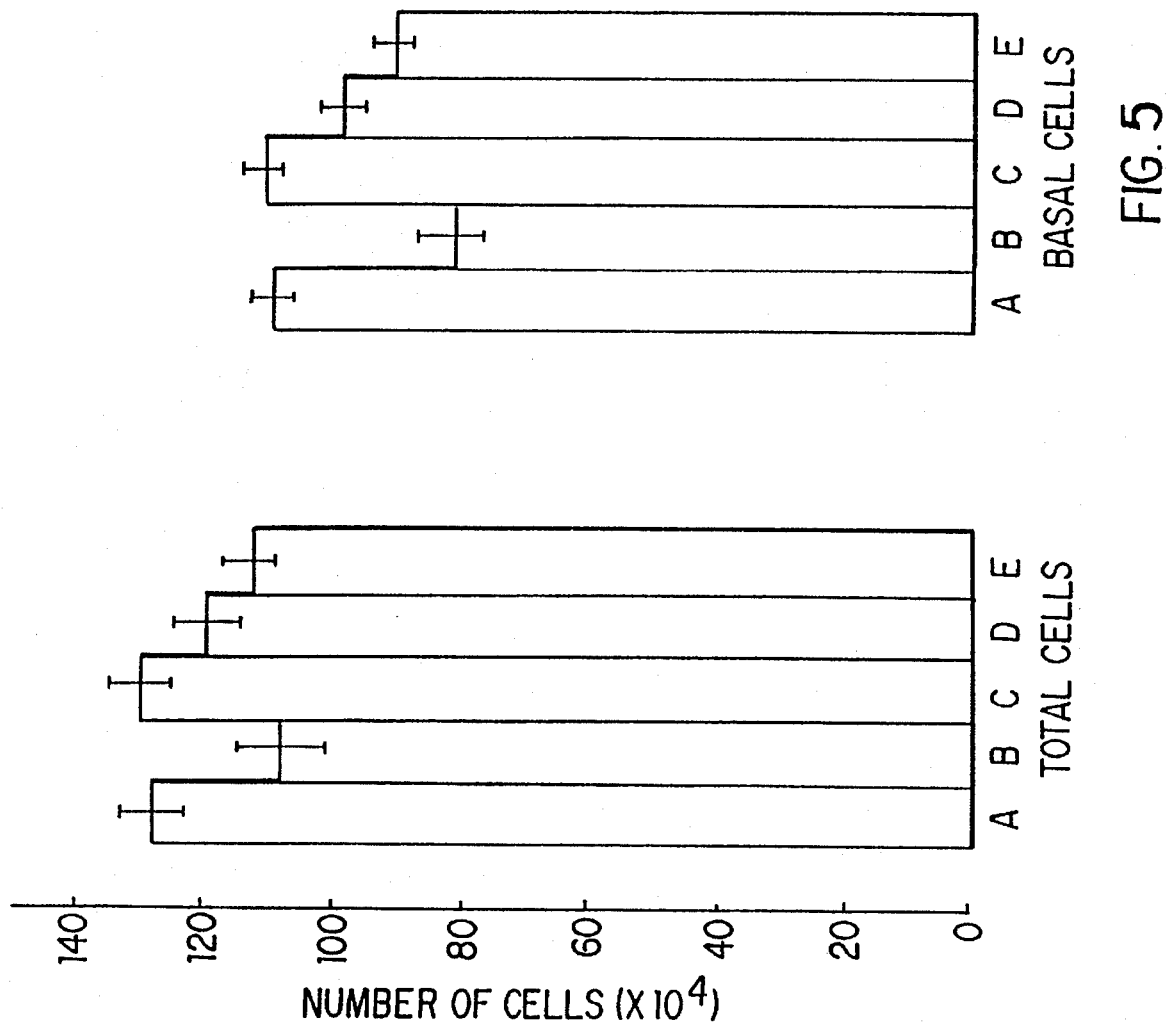

The peptides used in the methods of the invention are all easily synthesized, using recombinant DNA or solid phase peptide synthesis techniques, and some are available commercially as well, or can be derived from commercially available peptides. For example, there is reproduced below a section of the Bach Chem catalog, listing a number of available human, rat, and bovine analogs and fragments. (The Peninsula Laboratory catalog also lists available fragments.)

---

Hypercalcemia of Malignancy Factor (1–40)
(PTH-like Adenylate Cyclase-Stimulating Protein)
(ACSP)

H$_2$N—Ala—Val—Ser—Glu—His—Gln—Leu—Leu—His—Asp—Lys—Gly—Lys—Ser—Ile—Gln—Asp—
Leu—Arg—Arg—Arg—Phe—Phe—Leu—His—His—Leu—Ile—Ala—Glu—Ile—His—Thr—Ala—Glu—
Ile—Arg—Ala—Thr—Ser—OH
Parathyroid Hormone, Bovine (84 amino acids)

H$_2$N—Ala—Val—Ser—Glu—Ile—Gln—Phe—Met—His—Asn—Leu—Gly—Lys—His—Leu—Ser—Ser—
Met—Glu—Arg—Val—Glu—Trp—Leu—Arg—Lys—Lys—Leu—Gln—Asp—Val—His—Asn—Phe—
Val—Ala—Leu—Gly—Ala—Ser—Ile—Ala—Tyr—Arg—Asp—Gly—Ser—Ser—Gln—Arg—Pro—Arg—
Lys—Lys—Glu—Asp—Asn—Val—Leu—Val—Glu—Ser—His—Gln—Lys—Ser—Leu—Gly—Glu—Ala—
Asp—Lys—Ala—Asp—Val—Asp—Val—Leu—Ile—Lys—Ala—Lys—Pro—Gln—OH
[Tyr$^{63}$]-Parathyroid Hormone (63–84), Human H$_2$N—Tyr—Glu—Lys—Ser—Leu—Gly—Glu—Ala—Asp—Lys—Ala—Asp—Val—Asn—Val—Leu—Thr—
Lys—Ala—Lys—Ser—Gln—OH
Parathyroid Hormone (64–84), Human H$_2$N—Glu—Lys—Ser—Leu—Gly—Glu—Ala—Asp—Lys—Ala—Asp—Val—Asn—Val—Leu—Thr—Lys—
Ala—Lys—Ser—Gln—OH
[Tyr$^{69}$]-Parathyroid Hormone (69–84), Human H$_2$N—Tyr—Ala—Asp—Lys—Ala—Asp—Val—Asn—Val—Leu—Thr—Lys—Ala—Lys—Ser—Gln—OH
Parathyroid Hormone (70–84), Human H$_2$N—Ala—Asp—Lys—Ala—Asp—Val—Asn—Val—Leu—Thr—Lys—Ala—Lys—Ser—Gln—OH
Human Bone Gla Protein (37–49) (BGP 37–49)

H$_2$N—Gly—Phe—Gln—Glu—Ala—Tyr—Arg—Arg—Phe—Tyr—Gly—Pro—Val—OH
Ret Poser, J. W. et al., (1980) PNAS 255:8685
[Tyr$^{38}$, Phe$^{42,46}$]-Human Bone Gla Protein (38–49)

H$_2$N—Tyr—Gln—Glu—Ala—Phe—Arg—Arg—Phe—Phe—Gly—Pro—Val—OH
Human Bone Gla Protein (45–49)

H$_2$N—Phe—Tyr—Gly—Pro—Val—OH
Parathyroid Hormone, Human (84 amino acids)

H$_2$N—Ser—Val—Ser—Glu—Ile—Gln—Leu—Met—His—Asn—Leu—Gly—Lys—His—Leu—Asn—Ser—
Met—Glu—Arg—Val—Glu—Trp—Leu—Arg—Lys—Lys—Leu—Gln—Asp—Val—His—Asn—Phe—Val—
Ala—Leu—Gly—Ala—Pro—Leu—Ala—Pro—Arg—Asp—Ala—Gly—Ser—Gln—Arg—Pro—Arg—Lys—
Lys—Glu—Asp—Asn—Val—Leu—Val—Glu—Ser—His—Glu—Lys—Ser—Leu—Gly—Glu—Ala—Asp—
Lys—Ala—Asp—Val—Asn—Val—Leu—Thr—Lys—Ala—Lys—Ser—Gln—OH
Ret Kimura, T. et al., (1983) SBRC 114>483; Fairwell, T. et al, (1983) Biochemistry 22:2691
Parathyroid Hormone, Rat (84 amino acids)

H$_2$N—Ala—Val—Ser—Glu—Ile—Gln—Leu—Met—His—Asn—Leu—Gly—Lys—His—Leu—Ala—Ser—
Val—Glu—Arg—Met—Gln—Trp—Leu—Arg—Lys—Lys—Leu—Gln—Asp—Val—His—Asn—Phe—Val—
Ser—Leu—Gly—Val—Gln—Met—Ala—Ala—Arg—Glu—Gly—Ser—Tyr—Gln—Arg—Pro—Thr—Lys—
Lys—Glu—Asp—Asn—Val—Leu—Val—Asp—Gly—Asn—Ser—Lys—Ser—Leu—Gly—Glu—Gly—Asp—
Lys—Ala—Asp—Val—Asp—Val—Leu—Val—Lys—Ala—Lys—Ser—Gln—OH
Ret Heinrich, G. et al., (1984) J. Biol. Chem. 258:3320
Parathyroid Hormone (1–34), Bovine H$_2$N—Ala—Val—Ser—Glu—Ile—Gln—Phe—Met—His—Asn—Leu—Gly—Lys—His—Leu—Ser—Ser—
Met—Glu—Arg—Val—Glu—Trp—Leu—Arg—Lys—Lys—Leu—Gln—Asp—Val—His—Asn—Phe—OH
Ret Tregear, G. W. et al., (1977) Biochemistry 16:2817
Parathyroid Hormone (1–34), Human H$_2$N—Ser—Val—Ser—Glu—Ile—Gln—Leu—Met—His—Asn—Leu—Gly—Lys—His—Leu—Asn—Ser—
Met—Glu—Arg—Val—Glu—Trp—Leu—Arg—Lys—Lys—Leu—Gln—Asp—Val—His—Asn—Phe—OH Ret Takai, T. et al., (1978) Peptide Chemistry
Parathyroid Hormone (1–34) Biotinyl, Human Biotin—Ser—Val—Ser—Glu—Ile—Gln—Leu—Met—His—Asn—Leu—Gly—Lys—His—Leu—Asn—
Ser—Met—Glu—Arg—Val—Glu—Trp—Leu—Arg—Lys—Lys—Leu—Gln—Asp—Val—His—Asn—
Phe—OH
Parathyroid Hormone (1–34), Rat $H_2N$—Ala—Val—Ser—Glu—Ile—Gln—Leu—Met—His—Asn—Leu—Gly—Lys—His—Leu—Ala—Ser—
Val—Glu—Arg—Met—Gln—Trp—Leu—Arg—Lys—Lys—Leu—Gln—Asp—Val—His—Asn—Phe—OH
Ret Keutmana H. T. et al., (1984) abstract, ASBIJR Cont.
[$Nle^{8,18}$, $Tyr^{34}$]-Parathyroid Hormone (1–34), Amide, Bovine $H_2N$—Ala—Val—Ser—Glu—Ile—Gln—Phe—Nle—His—Asn—Leu—Gly—Lys—His—Leu—Ser—Ser—
Nle—Glu—Arg—Val—Glu—Trp—Leu—Arg—Lys—Lys—Leu—Gln—Asp—Val—His—Asn—Tyr—$NH_2$
Ret Colivera, M. D. et al., (1981) J. Biol. Chem. 256:10,555;
Rosenblatt, M. et al., (1977) Endocr. Res. Comm. 4:115;
Rosenblatt, M. et al., (1976) J. Biol. Chem. 251:150
[$Nle^{8,18}$, $Tyr^{34}$]-Parathyroid Hormone (1–34), Human $H_2N$—Ser—Val—Ser—Glu—Ile—Gln—Leu—Nle—His—Asn—Leu—Gly—Lys—His—Leu—Asn—Ser—
Nle—Glu—Arg—Val—Glu—Trp—Leu—Arg—Lys—Lys—Leu—Gln—Asp—Val—His—Asn—Tyr—OH
[$Nle^{8,21}$, $Tyr^{34}$]-Parathyroid Hormone (1–34), Amide, Rat $H_2N$—Ala—Val—Ser—Glu—Ile—Gln—Leu—Nle—His—Asn—Leu—Gly—Lys—His—Leu—Ala—Ser—
Val—Glu—Arg—Nle—Gln—Trp—Leu—Arg—Lys—Lys—Leu—Gln—Asp—Val—His—Asn—Tyr—$NH_2$
[$Tyr^1$]-Parathyroid Hormone (1–34), Human $H_2N$—Tyr—Val—Ser—Glu—Ile—Gln—Leu—Met—His—Asn—Leu—Gly—Lys—His—Leu—Asn—Ser—
Met—Glu—Arg—Val—Glu—Trp—Leu—Arg—Lys—Lys—Leu—Gln—Asp—Val—His—Asn—Phe—OH
Parathyroid Hormone (1–38), Human $H_2N$—Ser—Val—Ser—Glu—Ile—Gln—Leu—Met—His—Asn—Leu—Gly—Lys—His—Leu—Asn—Ser—
Met—Glu—Arg—Val—Glu—Trp—Leu—Arg—Lys—Lys—Leu—Gln—Asp—Val—His—Asn—Phe—
Val—Ala—Leu—Gly—OH
Ret Heach, R. D. et al., (1984) Morm. Metada. Res. 16:558
Parathyroid Hormone (1–44), Human $H_2N$—Ser—Val—Ser—Glu—Ile—Gln—Leu—Met—His—Asn—Leu—Gly—Lys—His—Leu—Asn—Ser—
Met—Glu—Arg—Val—Glu—Trp—Leu—Arg—Lys—Lys—Leu—Gln—Asp—Val—His—Asn—Phe—Val—
Ala—Leu—Gly—Ala—Pro—Leu—Ala—Pro—Arg—OH
Ret Kimura, T. et al., (1981) Biopolymers 20:1823
Parathyroid Hormone (3–34), Bovine $H_2N$—Ser—Glu—Ile—Gln—Phe—Met—His—Asn—Leu—Gly—Lys—His—Leu—Ser—Ser—Met—Glu—
Arg—Val—Glu—Trp—Leu—Arg—Lys—Lys—Leu—Gln—Asp—Val—His—Asn—Phe—OH
Ret Lowik, C. et al., (1985) Cell Calcium 6:311
[$Nle^{8,18}$, $Tyr^{34}$]-Parathyroid Hormone (3–34), Amide, Bovine $H_2N$—Ser—Glu—Ile—Gln—Phe—Nle—His—Asn—Leu—Gly—Lys—His—Leu—Ser—Ser—Nle—Glu—
Arg—Val—Glu—Trp—Leu—Arg—Lys—Lys—Leu—Gln—Asp—Val—His—Asn—Tyr—$NH_2$
Ret Rosenblatt, M. et al., (1977) J. Biol. Chem. 252:5847
[$Nle^{8,18}$, $Tyr^{34}$]-Parathyroid Hormone (7–34), Amide, Bovine $H_2N$—Phe—Nle—His—Asn—Leu—Gly—Lys—His—Leu—Ser—Ser—Nle—Glu—Arg—Val—Glu—
Trp—Leu—Arg—Lys—Lys—Leu—Gln—Asp—Val—His—Asn—Tyr—$NH_2$
[$Tyr^{34}$]-Parathyroid Hormone (7–34), Amide, Bovine
(Parathyroid Hormone Antagonist)

$H_2N$—Phe—Met—His—Asn—Leu—Gly—Lys—His—Leu—Ser—Ser—Met—Glu—Arg—Val—
Glu—Trp—Leu—Arg—Lys—Lys—Leu—Gln—Asp—Val—His—Asn—Tyr—$NH_2$
Parathyroid Hormone (13–34), Human $H_2N$—Lys—His—Leu—Asn—Ser—Met—Glu—Arg—Val—Glu—Trp—Leu—Arg—Lys—Lys—Leu—
Gln—Asp—Val—His—Asn—Phe—OH
[$Tyr^{27}$]-Parathyroid Hormone (27–48), Human $H_2N$—Tyr—Leu—Gln—Asp—Val—His—Asn—Phe—Val—Ala—Leu—Gly—Ala—Pro—Leu—Ala—
Pro—Arg—Asp—Ala—Gly—Ser—OH
Parathyroid Hormone (28–48), Human $H_2N$—Leu—Gln—Asp—Val—His—Asn—Phe—Val—Ala—Leu—Gly—Ala—Pro—Leu—Ala—Pro—
Arg—Asp—Ala—Gly—Ser—OH
Ret Rosenblatt, M. et al., (1977) Biochemistry 16:2811
[$Tyr^{43}$]-Parathyroid Hormone (43–68), Human $H_2N$—Tyr—Arg—Asp—Ala—Gly—Ser—Gln—Arg—Pro—Arg—Lys—Lys—Glu—Asp—Asn—Val—Leu—
Val—Glu—Ser—His—Glu—Lys—Ser—Leu—Gly—OH Parathyroid Hormone (44–68), Human H₂N—Arg—Asp—Ala—Gly—Ser—Gln—Arg—Pro—Arg—Lys—Lys—Glu—Asp—Asn—Val—Leu—Val—
Glu—Ser—His—Glu—Lys—Ser—Leu—Gly—OH
Ret Rosenblatt, M. et al., (1977) J. Med. Chem. 20:1452

[Tyr⁵²]-Parathyroid Hormone (52–84), Human

H₂N—Tyr—Lys—Lys—Glu—Asp—Asn—Val—Leu—Val—Glu—Ser—His—Glu—Lys—Ser—Leu—Gly—
Glu—Ala—Asp—Lys—Ala—Asp—Val—Asn—Val—Leu—Thr—Lys—Ala—Lys—Ser—Gln—OH

Parathyroid Hormone (53–84), Human

H₂N—Lys—Lys—Glu—Asp—Asn—Val—Leu—Val—Glu—Ser—His—Glu—Lys—Ser—Leu—Gly—Glu—
Ala—Asp—Lys—Ala—Asp—Val—Asn—Val—Leu—Thr—Lys—Ala—Lys—Ser—Gln—OH
Ret Rosenblatt, M. et al., (1978) Endocrinology 103:978

When selecting a candidate peptide for a method of this invention, a preferred first step is to choose a peptide which includes a fragment which has at least 10%, and more preferably 50% or greater, homology with an 8 or greater amino acid long fragment within the amino terminal 34 amino acid region of human PTH or hypercalcemic factor. By "homology" is meant amino acid sequence identity. Because of the high degree of homology among human PTH and PTH of other species, non-human as well as human fragments or analogs can be used. Further, the fragment can be modified in any of a variety of standard chemical ways, e.g., the carboxy-terminal amino acid residue can be made into a terminal amide group; the amino-terminal residue can be modified with groups to, e.g., enhance lipophilicity; the peptide can be chemically glycosylated to increase solubility or in vivo half-life; and D-amino acids can be substituted for L-isomers in the peptide.

Candidate peptides are tested for suitability as inhibitors of cell proliferation and enhancers of differentiation using cultured human keratinocytes, as described below. Those peptides which inhibit proliferation and induce differentiation in cultured keratinocytes are those potentially useful as therapeutic agents in treating disorders, e.g., psoriasis and cancer, where suppression of cell proliferation is desired.

Candidate peptides may be tested for suitability as enhancers of cell proliferation using cultured human keratinocytes. Those peptides which block the effect of agonist peptides or 1,25(OH)₂D₃ on cultured keratinocyte proliferation are those potentially useful as therapeutic agents in treating disorders, e.g., wounds, burns, or skin ulcerations, where maintenance or stimulation of cell proliferation is desired.

Candidate peptides may be tested for their ability to enhance wound healing by carrying out a skin punch biopsy test, described below.

Candidate peptides may be tested for suitability as stimulators of hair growth using an in vitro hair growth assay, such as is described below. Those peptides which stimulate hair growth in vitro are those potentially useful for the stimulation of hair growth in vivo, e.g., for the stimulation or maintenance of hair growth during or following chemotherapy or to treat a form of alopecia, e.g., male pattern baldness.

Peptides which block antiproliferative compounds can also be useful in conjunction with chemotherapeutic agents in the treatment of cancer; many chemotherapeutic agents are effective only against dividing cells, and the blocking peptides can have the effect of inducing division of otherwise dormant cells, rendering them vulnerable to the chemotherapy. Blocking peptides can also be useful in promoting growth of new cells, e.g., skin cells, in topical skin creams. Differentiation-inducing peptides can be used as immunostimulants, by inducing maturation of monocytes and lymphocytes bearing PTH receptors, while blocking peptides can be used to inhibit lymphocyte maturation, and thus can be used to treat conditions, e.g., autoimmune diseases such as juvenile diabetes, rheumatoid arthritis, and allograft rejection, where mature lymphocytes are a causative agent.

Keratinocyte Culture

Keratinocytes were grown in culture as follows. NIH 3T3 cells were plated at $0.5 \times 10^5$ cells per 35-mm tissue-culture dish, and two days later were lethally irradiated with a cobalt-60 source (5000 rads). Keratinocytes were obtained from neonatal foreskin after overnight trypsinization at 4° C. and treatment with 0.02% EDTA. Keratinocytes were plated in 2 ml of serum-free medium per dish on the lethally irradiated 3T3 cells. Each experiment was performed on primary or secondary keratinocyte cultures obtained from different skin samples. The serum-free medium consisted of Dulbecco's Modified Eagle's Medium (DMEM) with high (1.8 mM) concentration of calcium (M. A. Bioproducts, Walkersville, Md.) containing 7 growth factors: epidermal growth factor (25 ng/ml); hydrocortisone (203 ng/ml); insulin (5 µg/ml); prostaglandin $E_1$ (50 ng/ml); transferrin (5 µg/ml prostaglandin $E_1$ (50 ng/ml); cholera toxin (0.1 µg/ml); (Sigma Chemical Co., St. Louis, Mo.); and selenous acid (2 ng/ml) (Collaborative Research, Lexington, Mass.). At one week in culture, hydrocortisone and cholera toxin were removed from the medium, and the dishes were washed with 0.02% EDTA to remove any remaining 3T3 cells.

Four peptides were tested, at various concentrations, in keratinocyte culture: CFF (1-34); PTH (1-34); PTH (3-34); and PTH (7-34). In addition, 1,25(OH)₂D₃ was tested, alone and in combination with PTH (7-34), and PTH (1-34) and PTH (7-34) were tested together.

Quantitation of Morphological Changes During Keratinocyte Differentiation

Beginning at one week in culture, groups of triplicate plates of keratinocytes were incubated with the aforementioned compounds or vehicle alone. After one week of dosing, the medium was removed from each culture and centrifuged, and the pellet was resuspended for the counting of the desquamated floater cells. A hemacytometer was used to count the different cell types under a phase-contrast microscope. The attached cells were then trypsinized for 30–40 min with 0.1 EDTA and 0.1% trypsin and then neutralized with medium. The keratinocytes were pelleted and resuspended in a known volume of medium. Duplicate aliquots were taken for counting the basal (small, rounded) and squamous (larger, irregular-shaped, flattened) cells. The remaining cells were pelleted and treated with 10 mM Tris-HCl (pH 7.4) with 1% beta-mercaptoethanol and 1% sodium dodecyl sulfate (SDS) at room temperature for 10 min. Only cells with cornified envelopes were present after this treatment.

Each culture was thus evaluated for its total cell content, number of basal cells, and cornified envelopes, as described above. As can be seen in FIGS. 2, 3, 4 and 5, $1,25(OH)_2D_3$ decreased in a dose-dependent manner decreased the total number of cells and the number of basal cells in the cultures. In a similar manner, PTH (1-34) at $10^{-8}$M and $10^{-7}$M, and PTH (3-34) at $10^{-10}$ and $10^{-8}$M significantly decreased the total number of basal cells, as did CFF (1-34) at $10^{-8}$M and $10^{-7}$M. PTH (7-34) at $10^{-8}$M and $10^{-7}$M had no effect. However, when $1,25(OH)_2D_3$ at $10^{-8}$M was co-incubated with PTH (7-34) at $10^{-7}$M, the PTH antagonist significantly decreased the response to $1,25(OH)_2D_3$. Similarly, when PTH (7-34) was co-incubated with hPTH (1-34) or CFF (1-34), the PTH (7-34) inhibited the effect of PTH (1-34) and CFF (1-34) on the total number of cells and total number of basal cells in the cultures.

Figure 6:
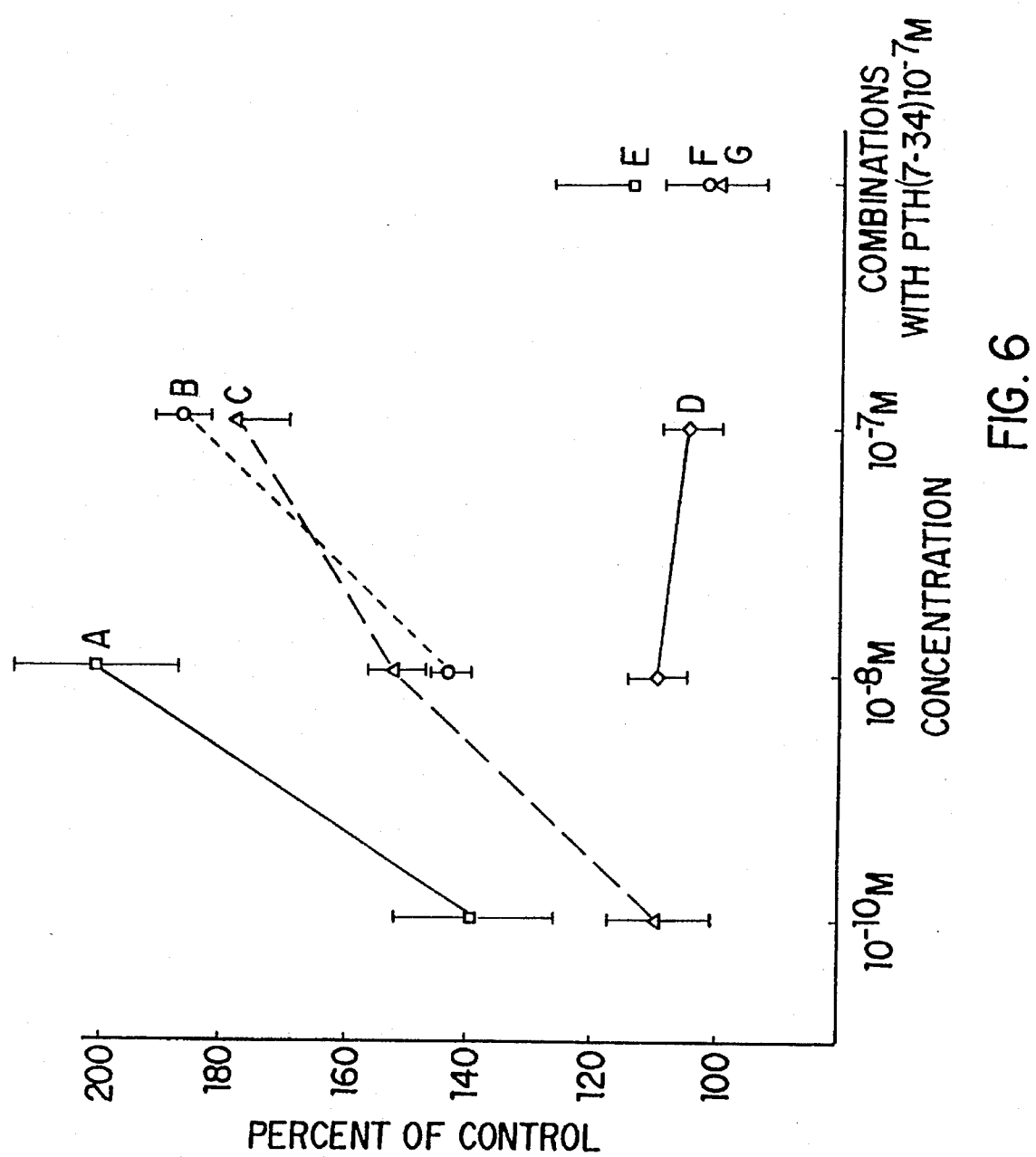
FIGS. 6 and 7 are graphs showing cell differentiation effects of peptides of the invention.
Figure 7:
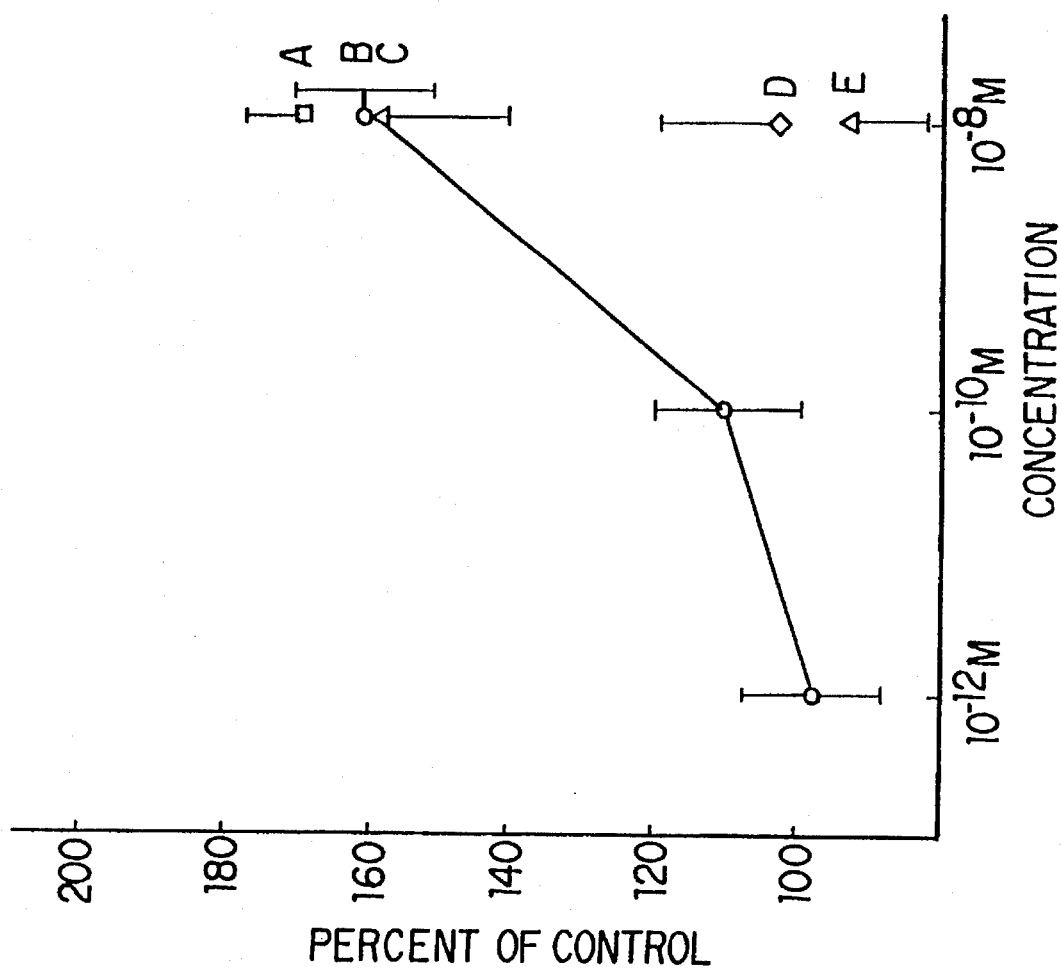

FIGS. 6 and 7 represent the percent of control of the total number of cornified envelopes observed in the cultures. As can be seen in FIG. 6, $1,25(OH)_2D_3$ increased, in a dose-dependent manner, the total number of cornified envelopes. Similarly, PTH (1-34), PTH (3-34), and CFF (1-34) also increased, in a dose-dependent manner, the number of cornified envelopes relative to the control cultures. PTH (7-34) alone at $10^{-8}$M and $10^{-7}$M had no effect. However, PTH (7-34) inhibited the effect of $1,25(OH)_2D_3$, PTH (1-34), and CFF (1-34) on cornified envelope development.

These results demonstrate that 1) PTH (1-34) is biologically effective in inhibiting the proliferation of cultured human keratinocytes and inducing terminal differentiation similar to $1,25(OH)_2D_3$, and is thus a candidate for use as a therapeutic for treatment of hyperproliferative diseases such as psoriasis and cancer; 2) CFF (1-34) and PTH (3-34) have the same effect as PTH (134) and are thus also candidates for hyperproliferative disease therapy; 3) PTH (7-34), an antagonist to PTH action, has substantially no effect on proliferation or terminal differentiation by itself, but can block the antiproliferative and differentiation-inducing activities of each of $1,25(OH)_2D_3$, PTH (1-34), and CFF (1-34), and thus is a candidate for repair therapies, e.g., treating burns, ulcerations, and wounds.

In vivo Skin Punch Assay

Male Sprague-Dawley rats were anesthetized by intraperitoneal injection of sodium pentobarbital, their dorsal skin shaved, and wounds made through the skin with a 6 mm dermal biopsy punch. Immediately after the biopsy, and each subsequent day for 3 days, groups of rats received topically 2.0 μg of human PTH (1-34) in normal saline or human PTH (7-34) in normal saline; a control group received normal saline without peptide. Four rats from each group were killed by asphyxiation in a chamber of carbon dioxide, and the extent of wound healing was evaluated as follows. Wounds were photographed with the wound surface perpendicular to the axis of the lens. After development of the film, wound images were projected on to paper at a fixed distance, traced with a pencil, and cut out with sharp scissors. The relative sizes of the wounds were assessed by weighing the cut-out paper tracings. Percent healing was calculated from the average decrease in wound area for each group.

Figure 8:
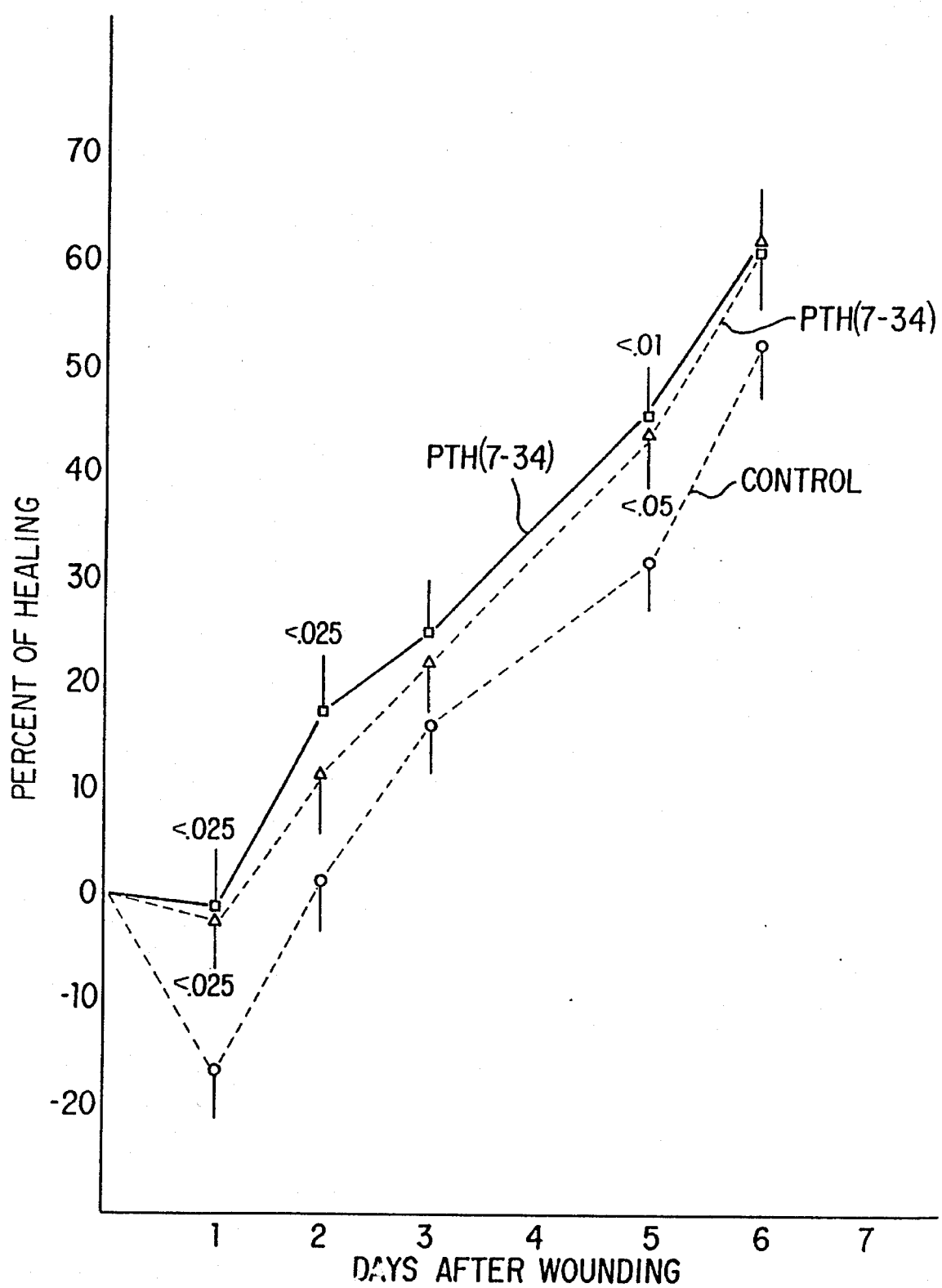
FIG. 8 is a graph showing wound healing effects of peptides of the invention.

FIG. 8 is a graphical representation of the percent wound healing exhibited by each of the test groups. Peptides PTH (7-34) and PTH (1-34) are biologically effective in enhancing wound healing in this in vivo assay and are thus candidates for use as therapeutic agents for enhancing the healing of wounds and for treating burns or skin ulcerations.

In vitro Hair Growth Assay

Candidate peptides may be screened for their ability to stimulate hair growth as follows. Hair is obtained from human subjects, preferably from a group of at least 18 subjects, including men, some of whom exhibit varying degrees of male pattern baldness, and women, and including subjects from different age groups. Hair is sampled from 4 sites of the scalp (frontal, occipital, temporal, and nuchal) and the following body areas: beard, axilla, pubic, chest, forearm, and leg, using the method described by van Scott et al. (J. Invest. Derm. 29: 197, 1957). Immediately after plucking, the hairs are placed in chilled Krebs-Ringer phosphate buffer, pH 7.4. Growing (anagen) and resting (telogen) hairs are differentiated either by gross examination or under low microscopic magnification. Generally, 2 to 4 anagen hairs and 10 to 30 telogen hairs are incubated in duplicate, in 2 ml. centrifuge tubes, in a total volume of 1 ml of incubation mixture consisting of Krebs-Ringer phosphate buffer, pH 7.4, glucose (9 mM), and candidate peptide; control incubation mixture lacks peptide. Samples are incubated with shaking at 37° C. in an air atmosphere. The reaction is stopped by the addition of 0.2 ml of absolute ethanol. Samples are stirred on a Vortex mixer and centrifuged in an International Centrifuge at 2000 rpm for 10 min. The supernatant is transferred to a 6×50 mm disposable Kimble culture tube, and the residue is extracted with 0.2 ml chloroform: methanol (2:1; v/v) by shaking for 15 min. at 37° C. in a water-bath. After centrifugation at 2000 rpm for 10 min., the supernatant is combined with that of the ethanol extraction. The samples are taken to dryness in air and redissolved in chloroform: methanol (2:1; v/v).

DNA content is determined by the method of Kissane and Robins (J. Biol. Chem. 233: 184, 1958) as modified by Santoianni and Ayala (J. Invest. Derm. 45: 99, 1965). After the second extraction with chloroform-methanol, the residue in the incubation tubes is dried gently under an air stream. Twenty μl of 1.5M aqueous diaminobenzoic acid-dihydrochloride is added, and the tubes are stirred briefly, capped, and heated for 30 min at 60° C. The reaction is stopped by adding 100 μl $HClO_4$. The mixture is stirred again, and a 100 μl aliquot is pipetted into fluorometric cuvettes containing 1 ml 0.6N $HClO_4$. Fluorescence is asssayed on an Aminco-Bowman Spectrofluorometer with the excitation wavelength set at 396 nm and the emission wavelength at 196 nm. Salmon sperm DNA (Sigma Corp., St. Louis, Mo.) is used as the standard. Routinely, standards containing 0.1, 0.4, 0.8, 1.2, 1.6, and 3.2 μg of DNA, and a blank are read with the samples.

Increased DNA content in a sample incubated in peptide-containing solution, relative to DNA content of a control sample, is taken as an indication that the peptide possesses in vitro hair growth-stimulatory activity.

Use

The peptides are administered in therapeutically effective amounts to people in need of them. Generally, the peptides are administered mixed with a pharmaceutically acceptable carrier substance, e.g., magnesium carbonate or lactose. The composition can be in the form of a pill, tablet, capsule, liquid, or sustained release tablet for oral administration; or a liquid for nasal, intravenous, subcutaneous, parenteral, or intraperitoneal administration. In addition, the compounds, can be used in a pharmacologically inert topical carrier such as one comprising a gel, an ointment or a cream, including such carriers as water, glycerol, alcohol, propylene glycol, fatty alcohols, triglycerides, fatty acid esters or mineral oils. Other possible carriers are liquid petrolatum, isopropylpalmitate, polyethylene glycol ethanor 95%, polyoxyethylene monolaurate 5% in water, sodium lauryl sulfate 5% in water, and the like. Materials such as antioxidants, humectants, viscosity stabilizers and the like may be added, if necessary.

The compounds can also be administered by means of subcutaneous pumps, patches, tapes or by means of liposomal carriers. The peptides can be provided in the form of pharmaceutically acceptable salts. Examples of preferred salts are those of therapeutically acceptable organic acids, e.g., acetic, lactic, maleic, citric, malic, ascorbic, succinic, benzoic, salicylic, methanesulfonic, toluenesulfonic, or pamoic acid, as well as polymeric acids such as tannic acid or carboxymethyl cellulose, and salts with inorganic acids such as hydrohalic acids, e.g., hydrochloric acid, sulfuric acid, or phosphoric acid.

Dosage will be dependent upon the age, health, and weight of the recipient; kind of concurrent treatment, if any; frequency of treatment; and the nature of the effect desired. Generally, daily dosage will be from about 0.001 micrograms/kg to 10,000 micrograms/kg, preferably 0.1 to 10 micrograms per kg of body weight. Normally, from 0.1 to 1000 micrograms/kg per day, in one or more applications per day, will be effective to obtain the desired results.

Other embodiments are within the following claims.

What is claimed is:

1. A method of inhibiting proliferation or enhancing differentiation of a mammalian skin cell, said method comprising contacting a mammalian skin cell in need of inhibited proliferation or enhanced differentiation with a proliferation-inhibiting or differentiation-enhancing amount of a peptide selected from the group consisting of PTH (1-34), PTH (3-34) and CFF (1-34).

2. The method of claim 1, wherein said contacting comprises administering to a mammal.

3. The method of claim 1, wherein said peptide is PTH (1-34).

4. The method of claim 1, wherein said peptide is PTH (3-34).

5. The method of claim 1, wherein said peptide is CFF (1-34).

6. A method of treating hyperproliferative skin disorders in mammals, said method comprising administering to a mammal in need thereof a peptide selected from the group consisting of PTH (1-34), PTH (3-34) and CFF (1-34) in an amount effective to inhibit proliferation or enhance differentiation of skin cells of said mammal.

7. The method of claim 6 wherein said hyperproliferative skin disorder is psoriasis.

8. A method of inducing proliferation of a mammalian skin cell, said method comprising contacting a mammalian skin cell in need of enhanced proliferation with a proliferation-inducing amount of the peptide PTH (7-34).

9. The method of claim 8, wherein said contacting comprises administering to a mammal.

10. A method of enhancing healing of a wound in a mammal in need thereof, said method comprising contacting said mammal with a wound-healing enhancing amount of a peptide selected from the group consisting of PTH (1-34) and PTH (7-34).

11. A method of enhancing or maintaining hair growth in a mammal, said method comprising administering to a mammal in need thereof the peptide PTH (7-34) in an amount effective to enhance or maintain hair growth.

12. A method of stimulating epidermal regrowth in a mammal in need thereof, said method comprising administering to a mammal a skin growth enhancing amount of the peptide PTH (7-34).

* * * * *